United States Patent [19]

Wu et al.

[11] Patent Number: 4,592,774

[45] Date of Patent: Jun. 3, 1986

[54] HERBICIDAL ALPHA HETEROCYCLIC CARBINOL CARBAMATES, UREAS AND N-ALPHA-SUBSTITUTED ACETYLCARBAMATES

[75] Inventors: Tai-Teh Wu; Jamin Huang, both of Chapel Hill; David T. Manning, Raleigh, all of N.C.

[73] Assignee: Union Carbide Corporation, Danbury, Conn.

[21] Appl. No.: 564,376

[22] Filed: Dec. 22, 1983

[51] Int. Cl.$^4$ .................. C07D 263/58; C07D 277/68; A01N 43/76; A01N 43/78

[52] U.S. Cl. ............................................ 71/90; 71/88; 71/92; 548/152; 548/179; 548/180; 548/204; 548/205; 548/217; 548/235; 548/236; 548/323; 548/330; 548/342

[58] Field of Search ............... 548/179, 180, 152, 202, 548/204, 205, 217, 235, 236, 330, 323, 342; 71/90, 92, 88

[56] References Cited

U.S. PATENT DOCUMENTS 3,318,889 5/1967 Bywater et al. ................ 260/286.4

FOREIGN PATENT DOCUMENTS 0028355 5/1981 European Pat. Off. .
0037524 10/1981 European Pat. Off. .
0037525 10/1981 European Pat. Off. .
0037526 10/1981 European Pat. Off. .
0037527 10/1981 European Pat. Off. .

OTHER PUBLICATIONS

Auidon et al., Khim. Geterotskl Soedin Akad. Nauk Latv. SSR, 1965 (1) 64–68.
Ermolaeva et al., Khim. Farm Zh. 1 (1) 19, 1967.
Sycheva et al., Khim. Geterotsikl Soedin 1966(5) 690–693.
Emolaeva et al., Khim. Geterotskl Soedin 1967 (1) 84–84.

Primary Examiner—Robert Gerstl
Attorney, Agent, or Firm—Clement J. Vicari

[57] ABSTRACT

Novel heterocyclic carbinol carbamates, ureas and N-acetyl-carbamates are provided which exhibit primarily preemergence control of broadleaf weeds with good selectivity for corn and certain other crops.

23 Claims, No Drawings

HERBICIDAL ALPHA HETEROCYCLIC CARBINOL CARBAMATES, UREAS AND N-ALPHA-SUBSTITUTED ACETYLCARBAMATES

FIELD OF THE INVENTION

This invention relates in general to novel heterocyclic carbinol carbamates, ureas and N-substituted acetylcarbamates and their derivatives. The invention also relates to processes for the synthesis of the aforementioned compounds and the use of said compounds. In one aspect, this invention is directed to novel heterocyclic carbinol carbamates, ureas and N-substituted acetylcarbamates which exhibit primarily preemergence control of broadleaf weeds. In general, the compounds exhibited good selectivity towards corn and other crops.

BACKGROUND OF THE INVENTION

Prior to the present invention, several aromatic carbamate derivatives of benzoxazol-2-yl oxy compounds were known to exhibit herbicidal activity. However, there does not appear to be any common link in this knowledge from which one could predict herbicidal activity in other benzoxazoles, or for that matter, tetrahydrobenzoxazole, benzofuran or imidazole type structures. Additionally the ideal combination of properties relating to effective broad spectrum weed control with appropriate crop selectivity is still a much sought after goal.

Accordingly, it is an object of the present invention to provide novel heterocyclic alpha-substituted carbinol compounds and processes for their preparation which exhibit preemergence control of broadleaf weeds and may be applied safely to important crops. Specifically the compounds are novel heterocyclic alpha-substituted carbinol carbamates, ureas and N-alpha-substituted acetylcarbamates.

A further object of this invention is to provide herbicidal compositions comprised of a carrier and the novel compounds described herein as the active ingredient.

A still further object of the invention is to provide a process for controlling broadleaf weeds by applying to such weeds herbicidal compositions containing the novel compounds.

These and other objects will readily become apparent to these skilled in the art.

SUMMARY OF THE INVENTION

In its broad aspect, the invention relates to novel alpha heterocyclic carbinol carbamates, ureas and N-alpha-substituted acetylcarbamates; herbicidal compositions containing same; and processes for their preparation and use. The novel compounds of this invention can be represented by the following generic formula:

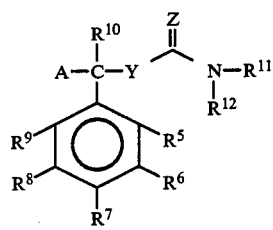

wherein the various substituents are identified below.

DETAILED DESCRIPTION OF THE INVENTION

As previously indicated, this invention is directed to the synthesis of novel alpha heterocyclic carbinol carbamates, ureas and N-alpha-substituted acetylcarbamates which exhibit excellent pre-emergence control of broadleaf weeds and a high degree of selectivity for corn and certain other crops.

The compounds of this invention are defined by the generic formula:

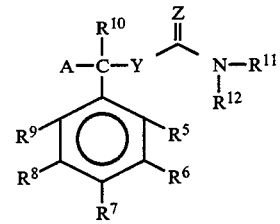

wherein

A is

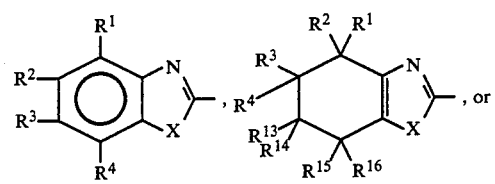

X is O, S or NR;
Y is O, S or NR;
Z is O, S or NR;
R is H or alkyl;
$R^1$ through $R^9$ inclusive and $R^{13}$ through $R^{16}$ inclusive are individually: hydrogen, halogen, alkyl, cycloalkyl, haloalkyl, halocycloalkyl, alkoxy, haloalkoxy, alkylthio, alkylamino, dialkylamino, nitro, cyano; or phenyl, phenoxy, or phenylthio unsubstituted or substituted with alkyl, alkoxy, alkylthio, halogen, nitro, cyano, amino, haloalkyl, alkylamino, dialkylamino, alkoxycarbonyl, alkylaminocarbonyl, dialkylaminocarbonyl, alkanoyl, aroyl, alkenyl, or alkynyl;
$R^{10}$ is hydrogen, alkyl, cycloalkyl, haloalkyl, halocycloalkyl, aryl, cyano, alkynyl; and
$R^{11}$ and $R^{12}$ are individually hydrogen, $C_1$-$C_3$ alkyl, $C_1$-$C_3$ haloalkyl, $C_1$-$C_3$ alkoxy, $C_1$-$C_3$ alkylthio; or phenoxy, phenylthio, or aryl; unsubstituted or substituted with halo, alkyl, alkoxy, nitro, cyano, alkylthio, alkylamino; alpha-haloacetyl, acetyl, alpha-alkylthioacetyl, alpha-aminoacetyl, alpha-alkoxyacetyl, alpha-phosphonoacetyl, phosphinoacetyl, phosphinylacetyl, phosphoacetyl, propionyl.

The preferred compounds of this invention are those in which

A is

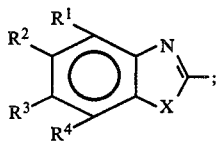

$R^1$ through $R^4$ inclusive are hydrogen; and
X, Y and Z are O.

The more preferred compounds of this invention are the preferred compounds
wherein
$R^7$ is hydrogen; and
$R^5$, $R^6$, $R^8$ and $R^9$ are individually hydrogen, $C_1$–$C_3$ alkyl, or halogen.

The most preferred compounds of the invention are the more preferred compounds wherein
$R^{11}$ and $R^{12}$ are individually hydrogen, $C_1$–$C_3$ alkyl, unsubstituted acetyl or halosubstituted acetyl.

It is accordingly, readily apparent from the scope of the preceding formulae that this invention encompasses a wide variety of novel heterocyclic carbinol carbamates, ureas and N-alpha-substituted acetylcarbamates. Tables A–C which follow, set forth certain subclasses within the broad generic formula and illustrate specific compounds falling within the particular classes. These examples will serve to illustrate but not limit the areas defined by this invention.

TABLE A

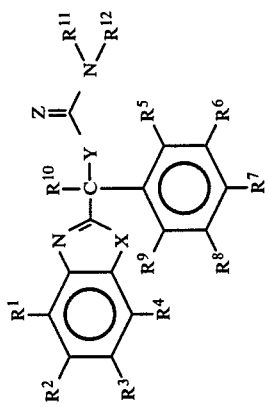

| X | Y | Z | R¹ | R² | R³ | R⁴ | R⁵ | R⁶ | R⁷ | R⁸ | R⁹ | R¹⁰ | R¹¹ | R¹² |
|---|---|---|----|----|----|----|----|----|----|----|----|-----|-----|-----|
| O | O | O | H | H | H | H | F | H | H | H | H | H | CH₃ | H |
| O | O | O | H | H | H | H | Br | H | H | H | H | H | CH₃ | H |
| O | O | O | H | H | H | H | F | H | H | H | F | H | CH₃ | H |
| O | O | O | H | H | H | H | Cl | H | H | H | F | H | CH₃ | H |
| O | O | O | H | H | H | H | CH₃ | H | H | H | CH₃ | H | CH₃ | H |
| O | O | O | H | H | H | H | CH₃ | OCH₃ | H | H | H | H | CH₃ | H |
| O | O | O | H | H | H | H | CH₃ | H | H | H | H | H | CH₃ | CH₃ |
| O | O | O | H | H | H | H | CH₃ | H | H | H | H | H | CH₃ | CH₃ |
| O | O | O | H | H | H | H | Cl | H | H | CH₃ | H | H | CH₃ | CH₃ |
| O | O | O | H | H | H | H | H | CH₃ | H | H | F | H | CH₃ | H |
| O | O | O | H | H | H | H | Cl | H | H | H | H | H | CH₃ | H |
| O | O | O | H | H | H | H | CH₃ | H | H | H | H | H | CH₃ | H |
| O | O | O | H | H | H | H | H | H | H | H | H | H | Et | H |
| O | O | O | H | H | H | H | Cl | H | H | H | H | H | Et | H |
| O | O | O | H | H | H | H | Cl | CH₃ | H | H | H | H | Et | H |
| O | O | O | H | H | H | H | Et | H | H | H | H | H | Et | H |
| O | O | O | H | H | H | H | CF₃ | H | H | H | F | H | CH₃ | H |
| O | O | O | H | H | H | H | H | CH₃ | F | H | H | H | CH₃ | H |
| O | O | O | H | H | H | H | CH₃ | CH₃ | Cl | H | H | H | CH₃ | H |
| O | O | O | H | H | H | H | H | H | CH₃ | H | H | H | CH₃ | H |
| O | O | O | H | H | H | H | F | F | H | H | H | H | CH₃ | H |
| O | O | O | H | H | H | H | CH₃ | CF₃ | H | H | H | H | CH₃ | H |
| O | O | O | H | H | H | H | H | H | H | H | H | H | CH₃ | H |
| O | O | O | H | Cl | H | H | Cl | H | H | H | H | H | CH₃ | H |
| O | O | O | H | Cl | H | H | Cl | H | H | H | H | H | CH₃ | H |
| O | O | O | H | Cl | H | H | Cl | H | H | H | F | H | CH₃ | H |
| O | O | O | H | Cl | H | H | CH₃ | H | H | H | H | H | CH₃ | H |
| O | O | O | H | CH₃ | CH₃ | H | Cl | H | H | H | H | H | CH₃ | H |
| O | O | O | H | CH₃ | CH₃ | H | CH₃ | H | H | H | H | H | CH₃ | H |
| O | O | O | H | H | H | H | Cl | H | H | H | F | H | CH₃ | H |
| O | O | O | H | H | Cl | H | CH₃ | H | H | H | H | H | CH₃ | H |
| O | O | O | H | H | H | H | CF₃ | H | H | H | H | H | CH₃ | H |
| S | O | S | H | Cl | H | H | Cl | H | H | H | H | H | CH₃ | CH₃ |
| O | S | O | H | H | H | H | Cl | H | H | H | H | H | CH₃ | H |
| O | O | O | H | H | H | H | H | H | H | H | H | H | CH₃ | H |

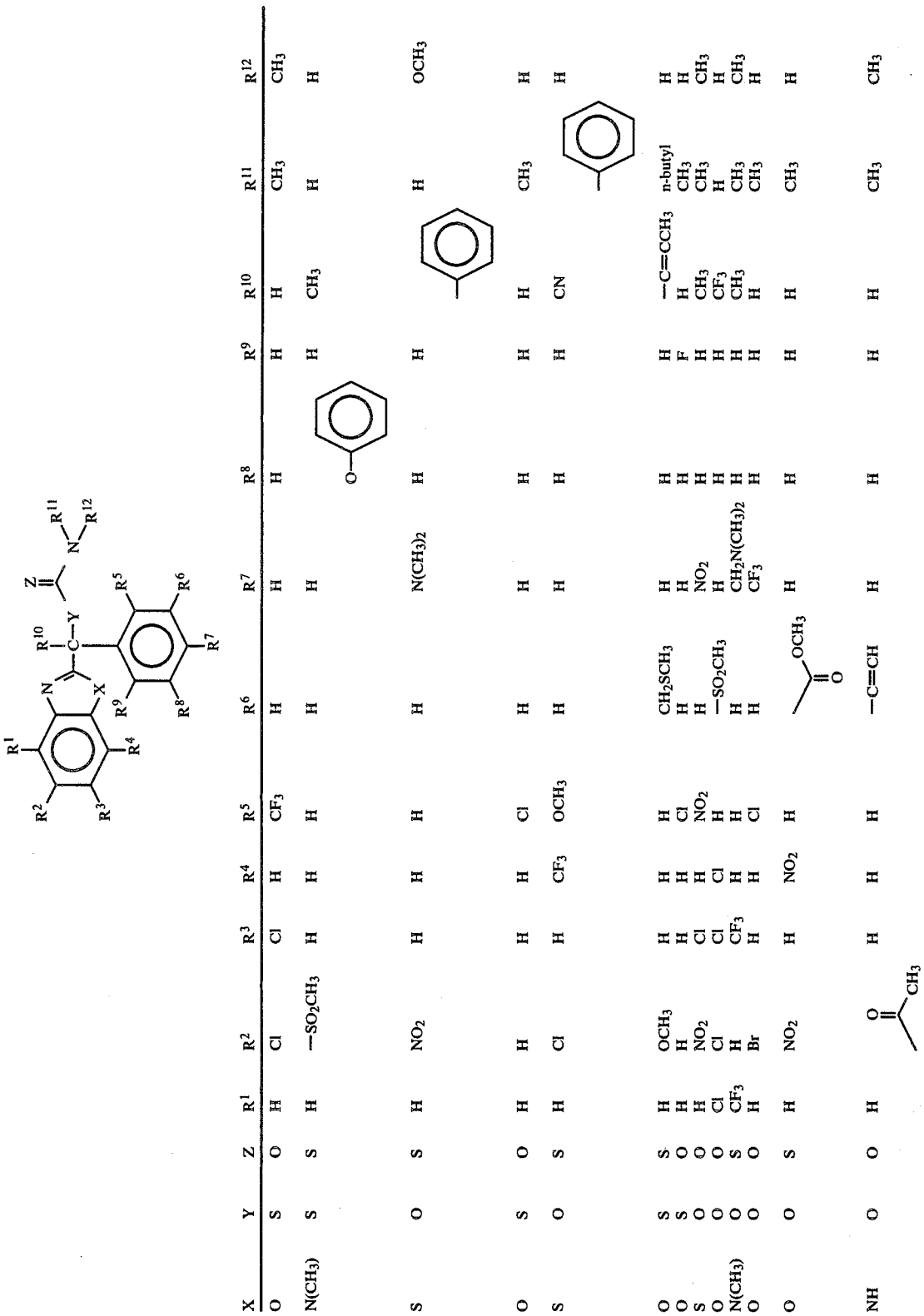

TABLE A-continued

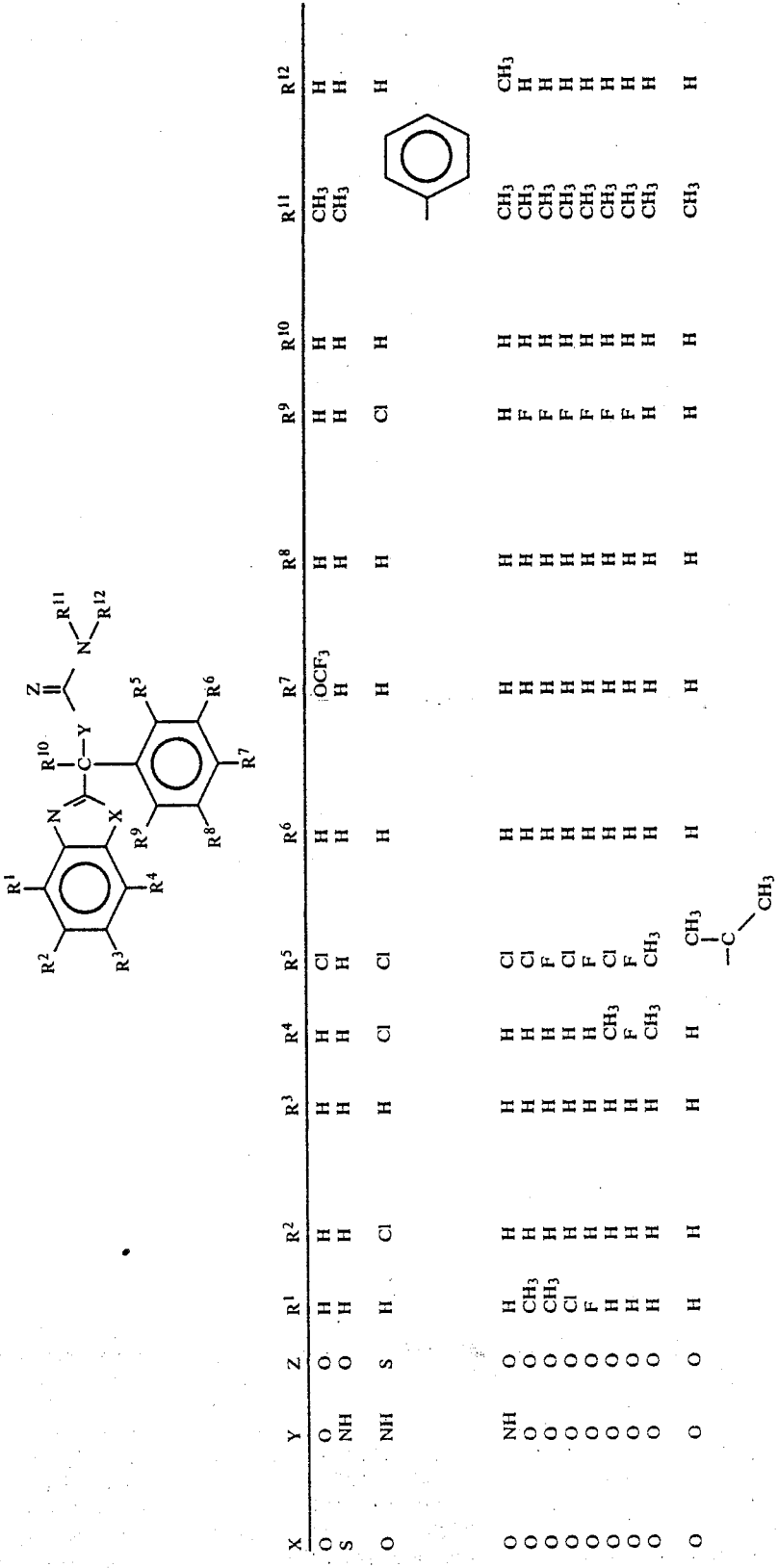

| X | Y | Z | R¹ | R² | R³ | R⁴ | R⁵ | R⁶ | R⁷ | R⁸ | R⁹ | R¹⁰ | R¹¹ | R¹² |
|---|---|---|----|----|----|----|----|----|----|----|----|-----|-----|-----|
| O | O | O | H | H | H | H | Cl | H | OCF₃ | H | H | H | CH₃ | H |
| S | NH | O | H | H | H | H | H | H | H | H | H | H | CH₃ | H |
| O | NH | S | H | Cl | H | Cl | Cl | H | H | H | Cl | H |  |  |
| O | O | O | H | H | H | H | Cl | H | H | H | H | H | CH₃ | CH₃ |
| O | O | O | CH₃ | H | H | H | Cl | H | H | H | F | H | CH₃ | H |
| O | O | O | CH₃ | H | H | H | F | H | H | H | F | H | CH₃ | H |
| O | O | O | Cl | H | H | H | Cl | H | H | H | F | H | CH₃ | H |
| O | O | O | F | H | H | CH₃ | F | H | H | H | F | H | CH₃ | H |
| O | O | O | H | H | H | F | Cl | H | H | H | F | H | CH₃ | H |
| O | O | O | H | H | H | CH₃ | F | H | H | H | F | H | CH₃ | H |
| O | O | O | H | H | H | H | CH₃ | H | H | H | H | H | CH₃ | H |
| O | O | O | H | H | H | H | —C(CH₃)₂—CH₃ | H | H | H | H | H | CH₃ | H |

(R¹¹–R¹² for row 3 are a phenyl (—N(phenyl)) group)

TABLE B

[Structure: benzoxazole with substituents R1-R4 on benzo ring, X in ring, C(R10)(phenyl with R5-R9)-Y-C(=Z)-N(R11)-C(=O)-CH2-R17]

| X | Y | Z | $R^1$ | $R^2$ | $R^3$ | $R^4$ | $R^5$ | $R^6$ | $R^7$ | $R^8$ | $R^9$ | $R^{10}$ | $R^{11}$ | $R^{17}$ |
|---|---|---|---|---|---|---|---|---|---|---|---|---|---|---|
| O | O | O | H | H | H | H | Cl | H | H | H | H | H | CH$_3$ | Cl |
| O | O | O | H | H | H | H | Cl | H | H | F | H | H | CH$_3$ | Cl |
| O | O | O | H | H | H | H | CH$_3$ | H | H | H | H | H | CH$_3$ | Cl |
| O | O | O | H | H | H | H | H | H | H | H | H | H | CH$_3$ | Cl |
| O | O | O | CH$_3$ | H | H | H | F | H | H | H | F | H | CH$_3$ | Cl |
| O | O | O | F | H | H | H | Cl | H | H | F | H | H | H | Cl |
| O | S | O | Cl | H | H | H | CH$_3$ | H | H | H | H | H | CH$_3$ | Cl |
| O | O | O | H | H | H | H | F | H | H | F | H | H | CH$_3$ | Cl |
| O | O | O | H | H | H | H | F | H | H | F | H | H | CH$_3$ | SCH$_3$ |
| O | O | O | H | H | H | H | F | H | H | H | Cl | H | H | SEt |
| O | O | O | H | H | H | H | F | H | H | H | Cl | H | CH$_3$ | N(CH$_3$)(CH$_3$)(CH$_3$) |
| O | S | O | H | H | H | H | F | H | H | H | Cl | H | H | Cl |

TABLE C

[Structure: partially hydrogenated benzoxazole with substituents R1-R4, R13-R16, X in ring, C(R10)(phenyl with R5-R9)-Y-C(=Z)-N(R11)(R12)]

| X | Y | Z | $R^1$ | $R^2$ | $R^3$ | $R^4$ | $R^5$ | $R^6$ | $R^7$ | $R^8$ | $R^9$ | $R^{10}$ | $R^{11}$ | $R^{12}$ | $R^{13}$ | $R^{14}$ | $R^{15}$ | $R^{16}$ |
|---|---|---|---|---|---|---|---|---|---|---|---|---|---|---|---|---|---|---|
| O | O | O | H | H | H | H | Cl | H | H | F | H | CH$_3$ | H | H | H | H | H |
| O | O | O | CH$_3$ | H | H | H | Cl | H | H | F | H | CH$_3$ | H | H | H | H | H |
| O | O | O | CH$_3$ | H | H | H | F | H | H | F | H | CH$_3$ | H | H | H | H | CH$_3$ |
| O | O | O | CH$_3$ | CH$_3$ | H | H | Cl | H | H | F | H | CH$_3$ | H | H | H | H | H |
| O | O | O | F | H | H | H | F | H | H | F | H | CH$_3$ | H | H | H | H | H |

The novel compositions of this invention can be prepared in two steps. Step I: preparation of appropriate alcohols, thiols, and amines, Step II: carbamoylation.

Preparation of appropriate alcohols and/or thiols can be achieved according to a variety of methods as illustrated by the following reaction schemes.

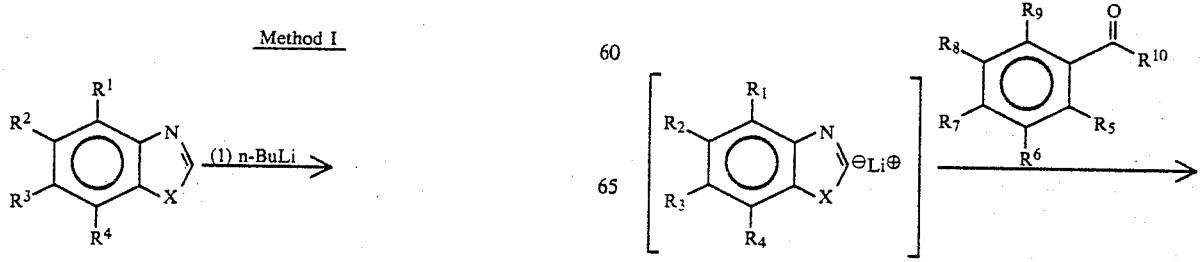

Method I

Method I

-continued

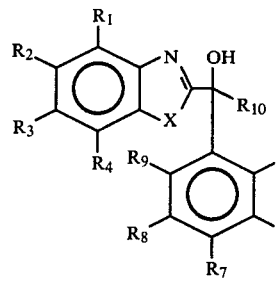

wherein: X, $R_1$, $R_2$, $R_3$, $R_4$, $R_5$, $R_6$, $R_7$, $R_8$, $R_9$, $R_{10}$ are as described previously.

Method II

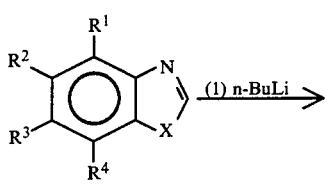

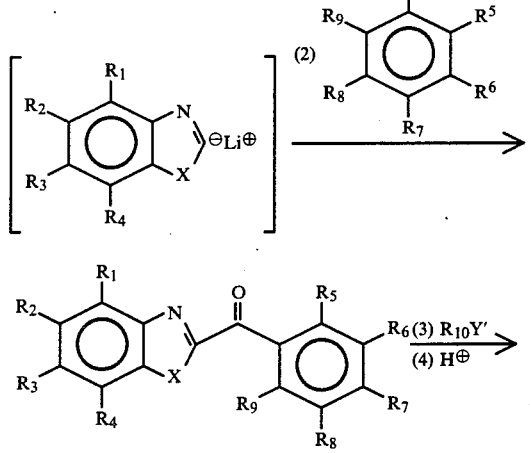

Wherein:
X' are $OCH_3$, $OCH_2CH_3$,

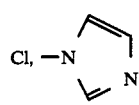

Y' are Li⊕, Na⊕, MgBr⊕
X, $R_1$, $R_2$, $R_3$, $R_4$, $R_5$, $R_6$, $R_7$, $R_8$, $R_9$, $R_{10}$ are as described previously.

Method III

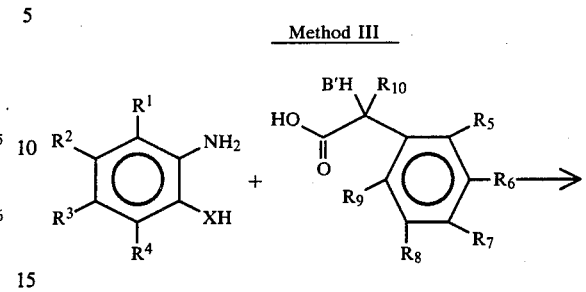

Wherein:
B' is O, S,
X, $R_1$, $R_2$, $R_3$, $R_4$, $R_5$, $R_6$, $R_7$, $R_8$, $R_9$, $R_{10}$ are as described previously.

Method IV

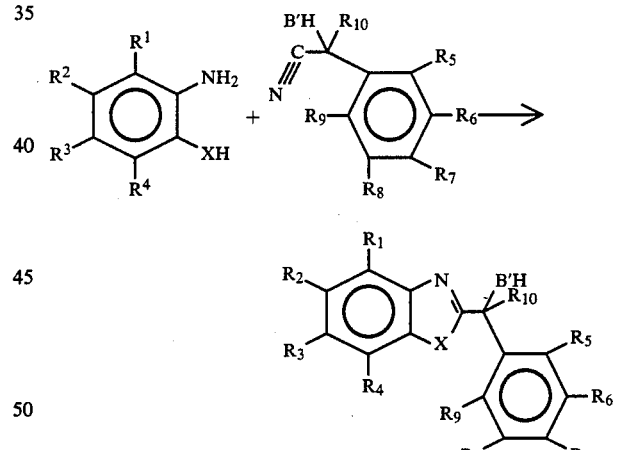

Wherein:
B' is O, S.
X, $R_1$, $R_2$, $R_3$, $R_4$, $R_5$, $R_6$, $R_7$, $R_8$, $R_9$, $R_{10}$ are as described previously.

Method V

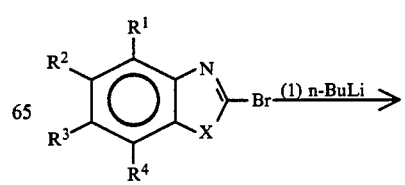

Method V

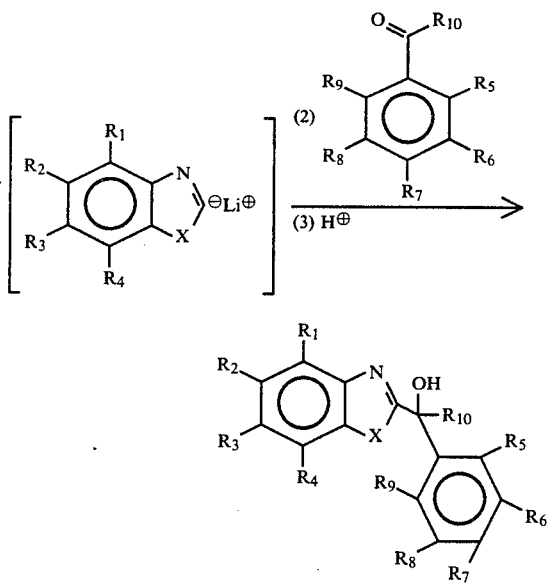

Wherein: X, R₁, R₂, R₃, R₄, R₅, R₆, R₇, R₈, R₉, R₁₀ are as described previously.

The substituted 2(benzoxazole)methanols illustrated in Method I can be effected by metallation of 1,3-benzoxazoles with one equivalent of n-butyllithium at −78° C., followed by the addition of appropriate aldehydes or ketones. This reaction may be performed in anhydrous diethyl ether or tetrahydrofuran. (Beraud and J. Metzger, *Bull. Soc. Chim. France*, 2072-4 (1962); H. Gilman and J. A. Beel, *J. Am. Chem. Soc.* 71, 2328-31 (1949).

Preparation of appropriate heterocycles can be achieved by the following reaction schemes.

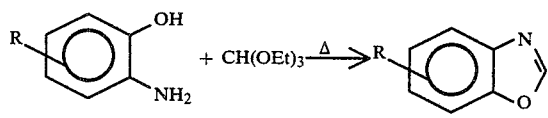

(Societe de Produits Chemiques et de Synthese. Fr. 1493401, Sept. 1, 1967; also CA 1968, Vol 69. 2856 g.)

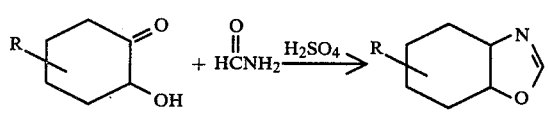

(Hellmut Bredereck and Rudolf Gompper, *Chem. Ber.* 87, 700-7 (1954))

The preparation of ketones in Method II can be achieved by metallation of 1,3-benzoxazoles as described in Method I, followed by addition of appropriate methyl benzoates (or ethyl benzoates, benzoyl chlorides, benzoyl imidazoles, phenyl nitriles). The desired carbinols can then be effected by nucleophilic addition of appropriate organometallic compounds (such as alkylithium, phenyllithium, Grignard reagents) or nitrile ion to the ketones.

The condensation reaction outlined in Method III can be accomplished using essentially equimolar ratios of the appropriate α-hydroxy acids (or α-thio-acids*) and o-aminophenols (or o-aminothiophenols, o-aminoanilines) in a variety of conditions. (*It can be prepared by the reaction of the appropriate α-bromophenylacetic acid with sodium sulfide nonahydrate (P. A. Levene; T. Mori; L. A. Mikeska, *J. Biochem* (Tokyo) 75, 337-365, 1927), followed by reduction of the disulfide with zinc in acetic acid. See: N. Wardell in "Chemistry of the Thiol Group", Patai, S., Ed.; Wiley; New York, 1974; Part 1, pp. 220-229).) This may be effected by azeotropically removing water via an inert, high-boiling organic solvent such as xylene. (F. Gualtiere, G. Brody, A. H. Fieldsteel and W. A. Skinner, *J. Med. Chem.* 14, 546-9 (1971).) It can also be achieved by refluxing the two components in an aqueous hydrochloric acid solution (Brit. 885,520 (1961), J. R. Geigy A-G.) or heating the two reagents in a sealed tube at an elevated temperature. (V. M. Zubarovskii; *Zhur, Obshchei Khim.* 21, 2199-205 (1951).)

The reaction illustrated in Method IV can be conducted using equimolar ratios of the appropriate α-hydroxy nitriles (or α-thio nitriles) and o-aminophenols (or o-aminothiophenols, o-aminoanilines) in refluxing methanol. (A. Banashek and M. H. Shchukina; *Zh. Obshch. Khim.* 32, 205-8 (1962).)

The reaction outlined under Method V can be accomplished by halogen-lithium exchange of 2-bromo-1,3-benzoxazoles with one equivalent of n-butyllithium at −78° C. The corresponding lithium salt can then react with a variety of aldehydes or ketones to form the desired alcohols. This reaction may be performed in anhydrous diethyl ether or tetrahydrofuran.

In general, the alcohols prepared in Method I to V are well-known compounds.

Preparation of appropriate amines can be achieved by the following reaction schemes.

Method VI

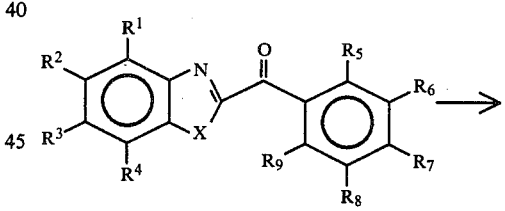

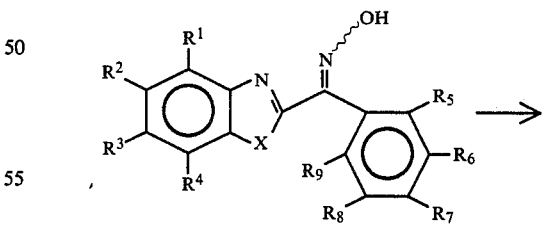

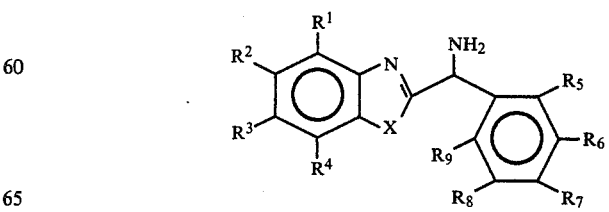

Wherein: X, R₁, R₂, R₃, R₄, R₅, R₆, R₇, R₈, R₉, are as described previously.

Method VII

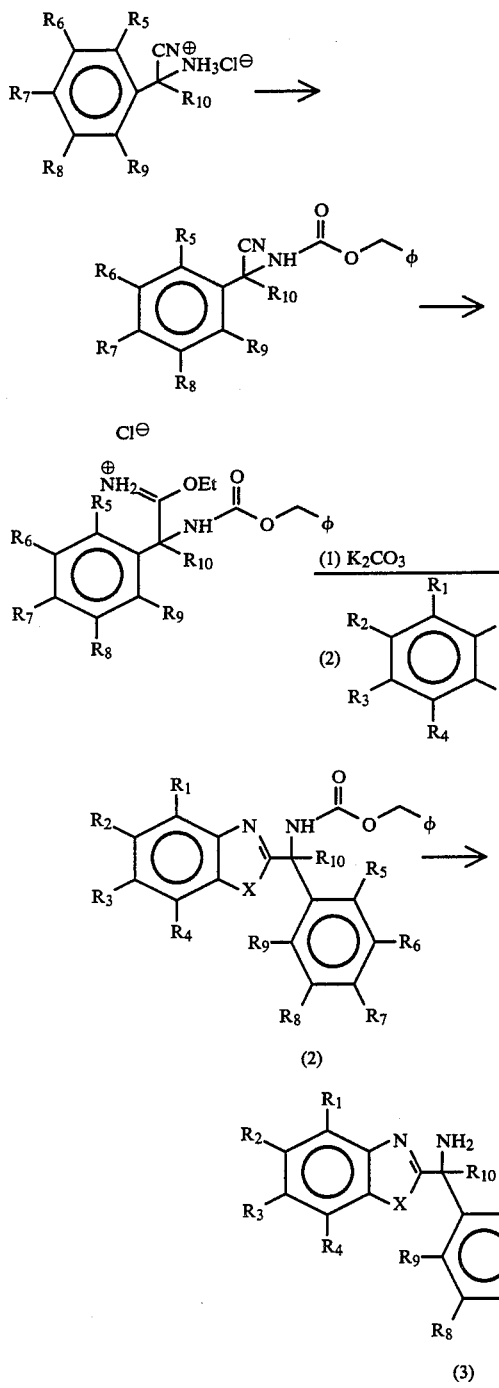

Wherein: X, R$_1$, R$_2$, R$_3$, R$_4$, R$_5$, R$_6$, R$_7$, R$_8$, R$_9$, R$_{10}$ are as described previously.

The reaction scheme outlined in Method VI demonstrates the preparation of amines. They can be achieved by formation of appropriate oximes, followed by reduction with powdered zinc in aqueous ammonia (V. V. Avidon and M. N. Shchukina; *Khim. Geterotsikl. Soedin., Akad. Nauk Latv.* SSR, 64–8 (1965); T. P. Sycheva, I. D. Kiseleva and M. N. Shchukina; Khim. Geterotsikl. Soedin., 690–3 (1966).)

The reaction scheme illustrated in Method VII can be effected by protecting the α-amino nitriles with a benzoyloxycarbonyl group. The nitriles are treated with dry hydrogen chloride in a mixture of absolute ethanol and absolute diethyl ether to yield the corresponding iminoether hydrochlorides. (A. J. Hill and I. Rabinowitz, *J. Am. Chem. Soc.* 48, 732–7 (1926); M. Mengelberg, *Chem. Ber.*, 89, 1185–95 (1956).)

Free iminoethers can be obtained by treatment of the iminoeher hydrochloride with an aqueous concentrated potassium carbonate solution. (Y. Hirotsu, T. Shiba, and T. Kaneko; *Bull. of Chem. Soc. of Japan*, 40, 2945–49 (1967).) Coupling of the imino ether with appropriate o-aminophenols, o-aminothiophenols or o-aminoanilines gives a protected amine (2) which can then be treated with 30% hydrogen bromide in acetic acid to afford the hydrobromide of the desired amine (3). (Y. Hirotsu, T. Shiba, and T. Kaneko; *Bull. of Chem. Soc. of Japan*, 43, 1564–67 (1970).) The amine (3) can be obtained by treatment with aqueous ammonia.

The carbamoylation illustrated in Method VIII can be achieved by reacting the appropriate alcohols, thiols, or amines and one equivalent of alkyl isocyanate (or aryl isocyanate, alkyl isothiocyanate, aryl isothiocyanate) in ethyl acetate or methylene chloride at room temperature. Catalytic amounts of dibutyltin diacetate can enhance the reaction rate.

Method VIII

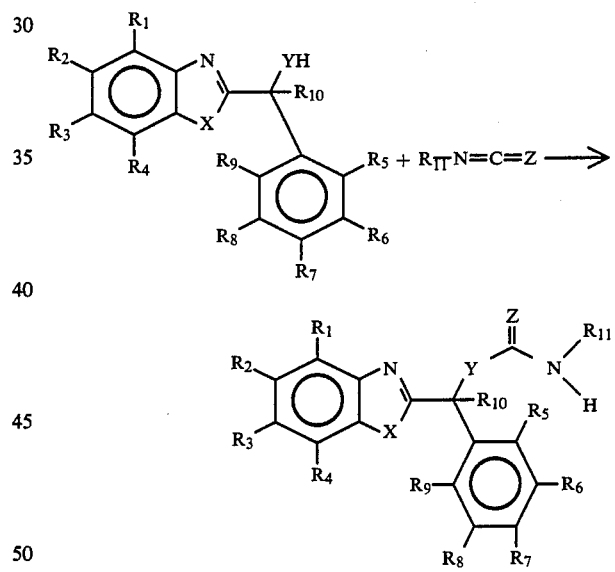

Wherein: X, Y, Z, R$_1$, R$_2$, R$_3$, R$_4$, R$_5$, R$_6$, R$_7$, R$_8$, R$_9$, R$_{10}$, R$_{11}$ are as described previously.

Method IX

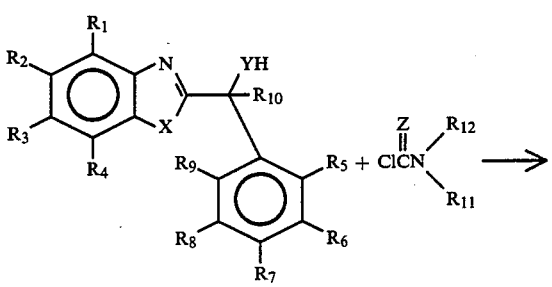

Method IX

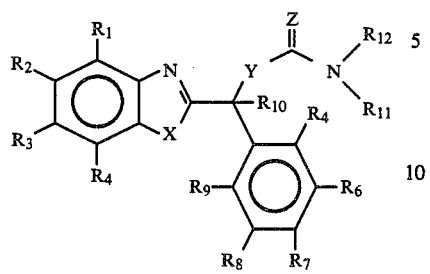

Wherein: X, Y, Z, $R_1$, $R_2$, $R_3$, $R_4$, $R_5$, $R_6$, $R_7$, $R_8$, $R_9$, $R_{10}$, $R_{11}$, $R_{12}$ are as described previously.

Method X

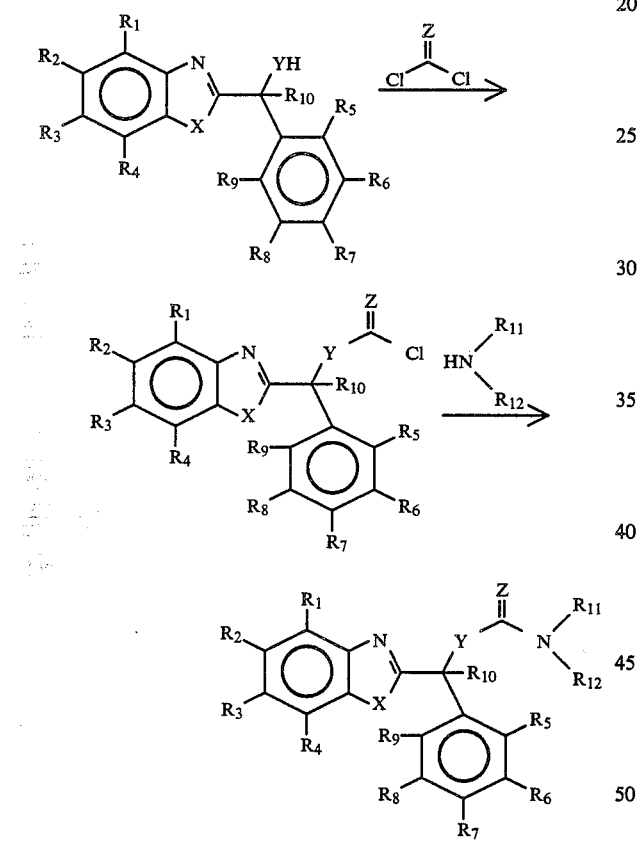

Wherein: X, Y, Z, $R_1$, $R_2$, $R_3$, $R_4$, $R_5$, $R_6$, $R_7$, $R_8$, $R_9$, $R_{10}$, $R_{11}$, $R_{12}$ are as described previously.

The reaction outlined in Method IX can be effected by using equimolar ratios of the alcohols (or thiols, amines) and appropriate carbamoyl chloride in the presence of an acid acceptor. Suitable acid acceptors are tertiary amine bases such as triethylamine, pyridine or N,N-dimethyl-4-aminopyridine. This reaction may be performed in a variety of refluxing solvents, such as acetonitrile, methyl chloride, ethylacetate.

The preparation of carbamates or ureas in Method X can be achieved by reaction of appropriate alcohols, thiols or amines with phosgene (or thiophosgene), followed by the addition of appropriate primary amines (or secondary amines) in the presence of an acid acceptor. Suitable acid acceptors are tertiary amine bases such as triethylamine or pyridine.

The synthesis of N-(α-haloacyl) carbamates or ureas in Method XI can be achieved by reacting the appropriate alcohols, thiols or amines with N-alpha-haloacyl-N-hydrocarbyl carbamoyl halides in the presence of 1.0 equivalent of an acid acceptor. Suitable acid acceptors are tertiary amine bases such as triethylamine, pyridine, or N,N-dimethyl-4-aminopyridine.

Method XI

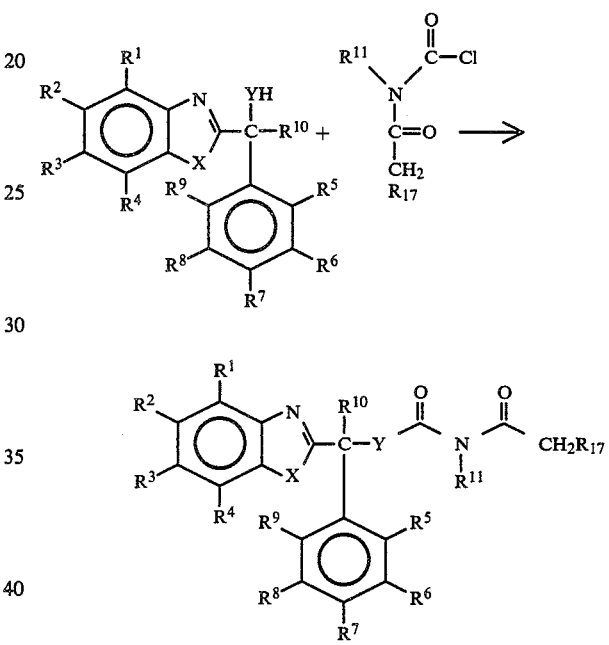

Wherein X, Y, Z, $R^1$, $R^2$, $R^3$, $R^4$, $R^5$, $R^6$, $R^7$, $R^8$, $R^9$, $R^{10}$ and $R^{11}$ are as described previously and $R^{17}$ is as described for $R^{13}$.

Method XII

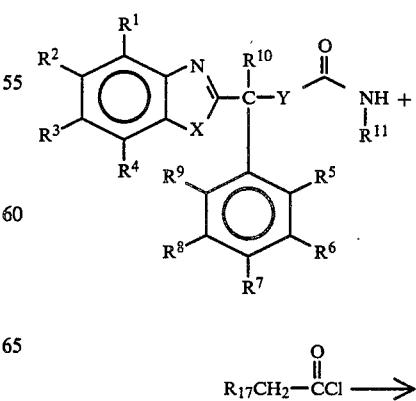

-continued
Method XII

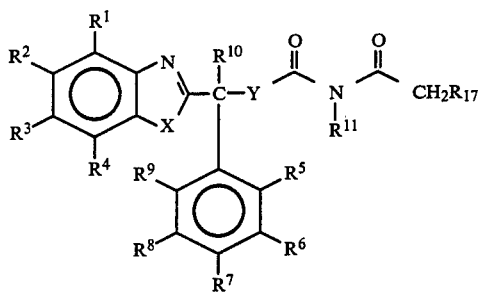

Wherein X, Y, Z, $R^1$, $R^2$, $R^3$, $R^4$, $R^5$, $R^6$, $R^7$, $R^8$, $R^9$, $R^{10}$ and $R^{11}$ are as described previously and $R^{17}$ is as described for $R^{13}$.

The reaction outlined in Method XII can be effected by using equimolar ratios of the appropriate carbamates (or ureas) and appropriate α-haloacylhalides in the presence of an acid acceptor. Suitable acid acceptors are tertiary amines bases such as triethylamine, pyridine or N,N-dimethyl-4-aminopyridine. The solvent used for this transformation may be methylene chloride, acetonitrile or ethyl acetate.

The following examples illustrate the best mode presently contemplated for the practice of this invention.

EXAMPLE I
2-(o-chloro-α-hydroxybenzyl)benzothiazole 47 mL of 1.6M-butyllithium in hexane was added dropwise to a solution of benzothiazole (10 g, from Aldrich) and diethyl ether (200 mL) at −78° C. under nitrogen. The red brown solution was stirred at −78° C. for 30 min., followed by the addition of a solution of o-chlorobenzaldehyde (10.8 g) and diethyl ether (100 mL) at −78° C. The mixture was then stirred at −78° C. for 2 hours before it was allowed to warm to room temperature and stirred at room temperature overnight.

It was then quenched by the addition of 7.5% NH4Cl aqueous solution (200 mL) and extracted with three portions of diethyl ether. The combined ether extracts were washed with brine, dried over Na2SO4, filtrate and concentrated in vacuo to yield a yellow solid. Recrystallization from hexane and ethyl acetate afforded 9.9 g of yellow needle crystals, mp 118°-120° C.

Anal. $C_{14}H_{10}ClNOS$: Calc. C, 60.97; H, 3.66; N, 5.08. Found C, 61.05; H, 3.55; N, 5.09.

EXAMPLE II
2(α-hydroxybenzyl)benzothiazole

A mixture of o-aminothiophenol (23.5 g) and dl-mandelic acid (25 g) was refluxed in xylene with a Dean-Stark tube for two days.

After cooling, the solution was washed with 1N HCl aqueous solution (500 mL), 5% Na2CO3 aqueous solution (500 mL) and brine. It was dried over MgSO4, filtered and concentrated in vacuo to yield a solid residue. Recrystallization from toluene afforded 16.6 g of white crystals.

Anal. $C_{14}H_{11}NOS$: Calc. C, 69.68; H, 4.60; N, 5.81. Found C, 70.10; H, 4.63; N, 5.78.

EXAMPLE III
2(α-aminobenzyl)benzothiazole

Ethyl benzoate (60.1 g, 0.4 mol.) in 200 mL of diethyl ether was added dropwise to 0.4 mol. of benzothiazolyllithium in 700 mL of diethyl ether (see Example I) at −78° C. and the mixture was then stirred 2 hours at −78° C. and overnight at room temperature. It was quenched by the addition of aqueous 10% NH4Cl solution and extracted with three portions of diethyl ether. The combined ether extracts were washed with brine, dried over Na2SO4, filtered, concentrated in vacuo and recrystallized from hexane and ethyl acetate to afford 41.5 g of light-brown crystals (phenyl 2-benzothiazolyl ketone).

A mixture of phenyl 2-benzothiazolyl ketone (35 g), hydroxylamine hydrochloride (10.5 g), pyridine (175 mL) and ethanol (175 mL) was refluxed for 4 hours. After cooling, the solution was concentrated in vacuo. The solid residue was washed with water, dried in vacuo, and 36.6 g of oxime was obtained.

The mixture of oxime (21.6 g), aqueous ammonia (800 mL) and ethanol (80 mL) was stirred with 16.7 g of powdered zinc at 50°-60° C. for 30 minutes, and another 2.5 g of powdered zinc was then added. The suspension was stirred at 50°-60° C. for 4 hours.

After cooling, the gray suspension mixture was extracted with three portions of methylene chloride. The combined methylene chloride extracts were dried over Na2SO4, filtered and concentrated in vacuo. Immediately after the addition of 1N HCl (200 mL) to the residue, a yellowish white solid was formed. It was filtered washed with water, then methylene chloride. 19.5 g of 2-(α-aminobenzyl)benzothiazole hydrochloride as a white solid was obtained.

The hydrochloride was stirred with aqueous ammonia and methylene chloride, and the aqueous layer was extracted with two portions of methylene chloride. The combined methylene chloride extracts were washed with brine, dried over Na2SO4, filtered and concentrated in vacuo. 13.1 g of white solid, as desired product, was obtained, mp. 68°-70° C.

Anal. $C_{14}12 N_2S$: Calc. C, 69.96; H, 5.03; N, 11.66. Found C, 69.88; H, 5.18N, 11.55.

EXAMPLE IV
N-methylcarbamoyloxy-2-(o-chloro-α-hydroxybenzyl)benzoxazole A mixture of 2-(o-chloro-α-hydroxybenzyl)benzoxazole (3 g), methyl isocyanate (1.06 mL), a catalytic amount of dibutyltin diacetate and methylene chloride (50 mL) was stirred at room temperature in a pressure bottle overnight, after which the mixture was concentrated in vacuo. The solid residue was partititioned between ethyl acetate-diethyl ether and water. The organic extract was dried over Na2SO4, filtered and concentrated in vacuo to yield the corresponding carbamate. Recrystallization from toluene afforded 2.2 g of crystals, mp. 116°-117° C.

Anal. $C_{16}H_{13}ClN_2O_3$: Calc. C, 60.67; H, 4.14; N, 8.85. Found C, 61.14; H, 4.17; N, 8.66.

EXAMPLE V

Preparation of α-(2-benzoxazolyl)-2-chlorophenyl-N-chloroacetyl-N-methylcarbamate To a mixture of 2-(0-chloro-α-hydroxybenzyl)benzoxazole (5.0 g, 0.019 mol) and N-chloroacetyl-N-methylcarbamyl chloride (3.23 g, 0.019 mol, 1.1 eq) in acetonitrile (150 mL) under a nitrogen atmosphere at 0° C. was added triethylamine (2.6 mL, 0.019 mol. 1 eq) in acetonitrile (75 mL). The resulting mixture was stirred at room temperature for 3 hours. The mixture was evaporated in vacuo. The residue was partitioned between $CH_2Cl_2$ and water. The organic layer was dried over anhydrous $Na_2SO_4$ and evaporated. The residue was purified by chromatography on silica gel using 100% $CH_2Cl_2$ to give 1.7 g (23%) of desired product as an oil.

Anal. $C_{18}H_{14}Cl_2N_2O_4$: Calc. C, 54.98; H, 3.59. Found C, 54.71; H, 3.78.

EXAMPLES 1-46

In a manner similar to that employed in the preceding examples, and using one of the synthesis schemes previously disclosed, other compounds of this invention were prepared. The identity of the substituents on the generic formulae and the analytical data are set forth in Tables I-IV below:

TABLE I
HERBICIDAL STRUCTURES

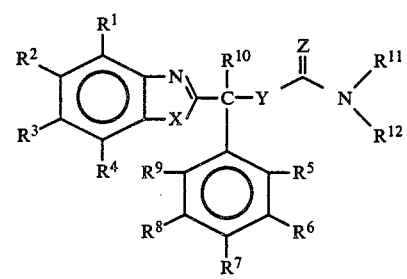

| Example | $R^1$ | $R^2$ | $R^3$ | $R^4$ | $R^5$ | $R^6$ | $R^7$ | $R^8$ | $R^9$ | $R^{10}$ | $R^{11}$ | $R^{12}$ | X | Y | Z |
|---|---|---|---|---|---|---|---|---|---|---|---|---|---|---|---|
| 1 | H | H | H | H | Cl | H | H | H | F | H | H | $CH_3$ | O | O | O |
| 2 | H | H | H | H | F | H | H | H | H | H | H | $CH_3$ | O | O | O |
| 3 | H | H | H | H | Br | H | H | H | H | H | H | $CH_3$ | O | O | O |
| 4 | H | H | H | H | Cl | H | H | H | F | H | H | $CH_3(CH_2)_3$ | O | O | O |
| 5 | H | H | H | H | $CH_3$ | H | H | $CH_3$ | H | H | H | $CH_3$ | O | O | O |
| 6 | H | H | H | H | H | F | H | H | H | H | H | $CH_3$ | O | O | O |
| 7 | H | H | H | H | H | $CH_3$ | H | H | H | H | H | $CH_3$ | O | O | O |
| 8 | H | H | H | H | H | $OCH_3$ | H | H | H | H | H | $CH_3$ | O | O | O |
| 9 | H | H | H | H | $CH_3$ | H | $CH_3$ | H | H | H | H | $CH_3$ | O | O | O |
| 10 | H | H | H | H | Cl | H | H | H | H | H | H | $CH_3$ | O | O | O |
| 11 | H | H | H | H | Cl | H | H | H | H | H | $CH_3$ | $CH_3$ | O | O | O |
| 12 | H | H | H | H | $CF_3$ | H | H | H | H | H | H | $CH_3$ | O | O | O |
| 13 | H | H | H | H | $CH_3$ | H | H | H | H | H | $CH_3$ | $CH_3$ | O | O | O |
| 14 | H | H | H | H | Cl | H | H | H | H | H | H | $CH_3CH_2$ | O | O | O |
| 15 | H | H | H | H | H | $CF_3$ | H | H | H | H | H | $CH_3$ | O | O | O |
| 16 | H | H | H | H | Cl | H | H | H | F | H | H | $CH_3CH_2$ | O | O | O |
| 17 | H | H | H | H | $CH_3$ | H | H | H | H | H | H | $CH_3CH_2$ | O | O | O |
| 18 | H | H | H | H | H | H | H | H | H | H | H | $CH_3CH_2$ | O | O | O |
| 19 | H | H | H | H | H | H | H | H | H | H | $CH_3$ | $CH_3$ | O | O | O |
| 20 | H | H | H | H | Cl | H | H | H | F | H | $CH_3$ | $CH_3$ | O | O | O |
| 21 | H | H | H | H | H | $CH_3$ | H | H | H | H | H | $CH_3CH_2$ | O | O | O |
| 22 | H | H | H | H | F | H | H | H | F | H | H | $CH_3$ | O | O | O |
| 23 | H | H | H | H | $CH_3$ | H | H | H | $CH_3$ | H | H | $CH_3$ | O | O | O |
| 24 | H | H | H | H | Cl | H | H | H | H | H | $CH_3$ | $ClCH_2CO$ | O | O | O |
| 25 | H | H | H | H | Cl | H | H | H | F | H | $CH_3$ | $ClCH_2CO$ | O | O | O |
| 26 | H | H | H | H | $CH_3$ | H | H | H | H | H | $CH_3$ | $ClCH_2CO$ | O | O | O |
| 27 | H | H | H | H | H | H | H | H | H | H | $CH_3$ | $ClCH_2CO$ | O | O | O |
| 28 | H | H | H | H | H | H | H | H | H | H | H | $CH_3$ | O | O | O |
| 29 | H | H | H | H | $CH_3$ | H | H | H | H | H | H | $CH_3$ | O | O | O |
| 30 | H | H | H | H | Cl | H | H | H | F | H | H | phenyl | O | O | O |
| 31 | H | $CH_3$ | H | H | Cl | H | H | H | F | H | H | $CH_3$ | O | O | O |
| 32 | H | $CH_3$ | H | H | Cl | H | H | H | H | H | H | $CH_3$ | O | O | O |
| 33 | H | $CH_3$ | H | H | $CH_3$ | H | H | H | H | H | H | $CH_3$ | O | O | O |
| 34 | H | Cl | H | H | Cl | H | H | H | H | H | H | $CH_3$ | O | O | O |
| 35 | H | Cl | H | H | Cl | H | H | H | F | H | H | $CH_3$ | O | O | O |
| 36 | H | Cl | H | H | $CH_3$ | H | H | H | H | H | H | $CH_3$ | O | O | O |
| 37 | H | Cl | H | H | F | H | H | H | H | H | H | $CH_3$ | O | O | O |
| 38 | H | H | $CH_3$ | H | $CH_3$ | H | H | H | H | H | H | $CH_3$ | O | O | O |
| 39 | H | H | $CH_3$ | H | Cl | H | H | H | F | H | H | $CH_3$ | O | O | O |
| 40 | H | H | H | H | Cl | H | H | H | H | H | H | $CH_3$ | S | O | O |
| 41 | H | H | H | H | $CH_2CH_3$ | H | H | H | H | H | H | $CH_3$ | O | O | O |
| 42 | H | H | H | H | H | H | H | H | H | H | H | $CH_3$ | S | O | O |
| 43 | H | H | H | H | $NO_2$ | H | H | H | H | H | H | $CH_3$ | S | O | O |
| 44 | H | H | H | H | $OCH_3$ | H | H | H | H | H | H | $CH_3$ | S | O | O |

TABLE I-continued
HERBICIDAL STRUCTURES

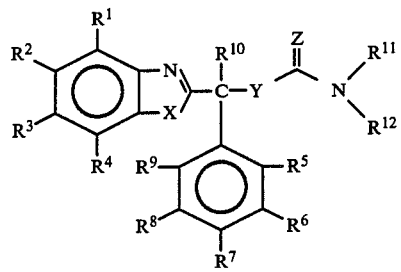

| Example | R¹ | R² | R³ | R⁴ | R⁵ | R⁶ | R⁷ | R⁸ | R⁹ | R¹⁰ | R¹¹ | R¹² | X | Y | Z |
|---|---|---|---|---|---|---|---|---|---|---|---|---|---|---|---|
| 45 | H | H | H | H | Cl | H | Cl | H | H | H | H | $CH_3$ | O | O | O |
| 46 | H | H | H | H | Cl | H | Cl | H | H | H | H | $CH_3$ | $NCH_3$ | O | O |
| 47 | H | H | H | H | Cl | H | Cl | H | H | H | H | $CH_3(CH_2)_3$ | O | O | O |
| 48 | H | H | H | H | H | Cl | Cl | H | H | H | H | $CH_3$ | O | O | O |
| 49 | H | H | H | H | Cl | H | Cl | H | H | H | $CH_3$ | $CH_3$ | O | O | O |
| 50 | H | H | H | H | Cl | H | H | H | Cl | H | H | $CH_3$ | O | O | O |
| 51 | H | H | H | H | Cl | H | H | H | Cl | H | $CH_3$ | $CH_3$ | O | O | O |
| 52 | H | H | H | H | H | H | H | H | H | H | H | $CH_3$ | S | NH | O |
| 53 | H | H | H | H | H | H | H | H | H | H | H | 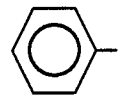 | S | NH | O |

TABLE II
HERBICIDAL STRUCTURES

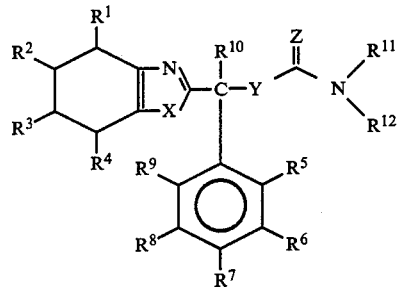

| Example | R¹ | R² | R³ | R⁴ | R⁵ | R⁶ | R⁷ | R⁸ | R⁹ | R¹⁰ | R¹¹ | R¹² | X | Y | Z |
|---|---|---|---|---|---|---|---|---|---|---|---|---|---|---|---|
| 54 | H | H | H | H | Cl | H | H | H | F | H | H | $CH_3$ | O | O | O |

TABLE III
HERBICIDAL STRUCTURES

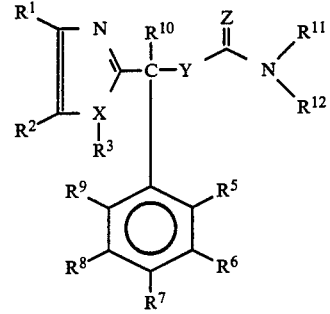

| Example | R¹ | R² | R³ | R⁵ | R⁶ | R⁷ | R⁸ | R⁹ | R¹⁰ | R¹¹ | R¹² | X | Y | Z |
|---|---|---|---|---|---|---|---|---|---|---|---|---|---|---|
| 55 | H | H | $CH_3$ | F | H | H | H | H | H | H | $CH_3$ | H | O | O |
| 56 | H | H | $CH_3$ | Cl | H | H | H | F | H | H | $CH_3$ | H | O | O |

TABLE IV
PHYSICAL PROPERTIES OF HERBICIDAL COMPOUNDS

| | | | Calculated | | | Found | | |
|---|---|---|---|---|---|---|---|---|
| Example | M.P. (°C.) | Formula | C | H | N | C | H | N |
| 1 | 134.5–136.5 | $C_{16}H_{22}ClFN_2O_3$ | 57.4 | 3.6 | 8.4 | 57.49 | 3.39 | 8.34 |
| 2 | 110.0–112.0 | $C_{16}H_{13}FN_2O_3$ | | | | | | |
| 3 | 130.0–131.5 | $C_{16}H_{13}BrN_2O_3$ | 53.21 | 3.63 | 7.76 | 53.61 | 3.89 | 7.72 |
| 4 | 97.0–98.0 | $C_{19}H_{18}ClFN_2O_3$ | 60.56 | 4.81 | 7.43 | 60.55 | 4.86 | 7.46 |
| 5 | 150.5–152.0 | $C_{18}H_{18}N_2O_3$ | 69.66 | 5.85 | 9.03 | 70.00 | 6.03 | 9.02 |
| 6 | 197.5–199.0 | $C_{16}H_{13}FN_2O_3$ | 64.00 | 4.36 | — | 64.83 | 4.29 | — |
| 7 | 125.5–127.0 | $C_{17}H_{16}N_2O_3$ | 68.91 | 5.44 | — | 68.71 | 5.55 | — |
| 8 | | $C_{17}H_{16}N_2O_4$ (ir (film) 3360, 2960, 1730, 1605, 1530, 1250, 1130 $cm^{-1}$) | | | | | | |
| 9 | 127.0–128.5 | $C_{18}H_{18}N_2O_3$ | 69.66 | 5.85 | — | 69.83 | 5.84 | — |
| 10 | 116–117 | $C_{16}H_{13}ClN_2O_3$ | 60.67 | 4.14 | 8.85 | 61.14 | 4.17 | 8.66 |
| 11 | 123.5–127.0 | $C_{17}H_{15}ClN_2O_3$ | 61.73 | 4.57 | — | 61.55 | 4.59 | — |
| 12 | 98.0–100.0 | $C_{17}H_{13}F_3N_2O_3$ | 58.29 | 3.74 | — | 57.95 | 3.80 | — |
| 13 | 139.5–142.5 | $C_{18}H_{18}N_2O_3$ | 69.66 | 5.85 | — | 69.60 | 5.98 | — |
| 14 | 106.5–108.5 | $C_{17}H_{15}ClN_2O_3$ | 61.73 | 4.57 | — | 61.91 | 4.65 | — |
| 15 | 117.5–119.5 | $C_{17}H_{13}F_3N_2O_3$ | 58.29 | 3.74 | — | 58.62 | 3.92 | — |
| 16 | 118.0–119.5 | $C_{17}H_{14}ClFN_2O_3$ | 58.55 | 4.05 | — | 58.43 | 4.26 | — |

TABLE IV-continued
PHYSICAL PROPERTIES OF HERBICIDAL COMPOUNDS

| | | | Calculated | | | Found | | |
|---|---|---|---|---|---|---|---|---|
| Example | M.P. (°C.) | Formula | C | H | N | C | H | N |
| 17 | 108–110 | $C_{18}H_{18}N_2O_3$ | 69.66 | 5.85 | — | 69.79 | 5.99 | — |
| 18 | 121.0–123.0 | $C_{17}H_{16}N_2O_3$ | 68.91 | 5.44 | — | 69.10 | 5.67 | — |
| 19 | 107–108 | $C_{17}H_{16}N_2O_3$ | 68.91 | 5.44 | — | 69.07 | 5.50 | — |
| 20 | — | $C_{17}H_{14}ClFN_2O_3$ | 58.55 | 4.05 | — | 58.12 | 4.15 | — |
| 21 | — | $C_{18}H_{18}N_2O_3$ | | | | NMR: δ 2.32(S,3H), $CH_3$ on phenyl ring | | |
| 22 | 138.5–139.5 | $C_{16}H_{12}F_2N_2O_3$ | 60.38 | 3.80 | — | 60.24 | 3.90 | — |
| 23 | 115.5–118.0 | $C_{18}H_{18}N_2O_3$ | 69.66 | 5.85 | | 69.40 | 6.11 | |
| 24 | — | $C_{18}H_{14}Cl_2N_2O_4$ | 54.98 | 3.59 | — | 54.71 | 3.78 | — |
| 25 | | $C_{18}H_{13}Cl_2FN_2O_4$ | 52.58 | 3.19 | — | 52.27 | 3.49 | — |
| 26 | | $C_{19}H_{17}ClN_2O_4$ | 61.21 | 4.60 | — | 69.85 | 4.60 | — |
| 27 | | $C_{18}H_{15}ClN_2O_4$ | 60.26 | 4.21 | — | 59.73 | 4.43 | — |
| 28 | Viscous oil | $C_{16}H_{14}N_2O_3$ | 68.08 | 5.00 | 9.93 | 69.08 | 4.64 | 9.02 |
| 29 | 114.0–115.5 | $C_{17}H_{16}N_2O_3$ | 68.91 | 5.44 | 9.45 | 69.43 | 5.62 | 9.45 |
| 30 | — | $C_{21}H_{14}ClFN_2O_3$ | 63.57 | 3.56 | 7.06 | 63.52 | 3.74 | 7.01 |
| 31 | 142.5–144.5 | $C_{17}H_{14}ClFN_2O_3$ | 58.55 | 4.05 | — | 58.56 | 4.11 | — |
| 32 | 127.5–129.0 | — | | | | | | |
| 33 | 138.0–139.0 | $C_{18}H_{18}N_2O_3$ | 69.66 | 5.85 | — | 69.84 | 5.87 | — |
| 34 | 111.5–113.0 | $C_{16}H_{12}Cl_2N_2O_3$ | 54.72 | 3.44 | — | 55.18 | 3.63 | — |
| 35 | 131.0–133.5 | $C_{16}H_{11}Cl_2FN_2O_3$ | 52.06 | 3.00 | — | 52.61 | 3.09 | — |
| 36 | 123–126 | $C_{17}H_{15}ClN_2O_3$ | 61.73 | 4.57 | — | 61.63 | 4.56 | — |
| 37 | 145–147 | $C_{16}H_{12}ClFN_2O_3$ | 57.41 | 3.61 | — | 57.24 | 3.73 | — |
| 38 | 119.0–121.0 | $C_{18}H_{18}N_2O_3$ | 69.66 | 5.85 | — | 70.12 | 5.98 | — |
| 39 | 115.0–117.5 | $C_{17}H_{14}FClN_2O_3$ | 58.55 | 4.05 | — | 58.93 | 4.16 | — |
| 40 | 117–119 | $C_{16}H_{13}ClN_2O_2S$ | 57.74 | 3.94 | 8.42 | 57.80 | 3.86 | 8.47 |
| 41 | — | $C_{18}H_{18}N_2O_3$ | 69.66 | 5.85 | — | 69.65 | 6.12 | — |
| 42 | 104–106 | $C_{16}H_{14}N_2O_2S$ | 64.40 | 4.73 | 9.39 | 64.48 | 4.95 | 9.03 |
| 43 | 139–142 | $C_{16}H_{13}N_3O_4S$ | 55.97 | 3.82 | 12.24 | 55.85 | 3.83 | 12.18 |
| 44 | 152–154 | $C_{17}H_{16}N_2O_3S$ | 62.17 | 4.91 | 8.53 | 61.50 | 4.78 | 8.52 |
| 45 | 137–138 | $C_{16}H_{12}Cl_2N_2O_3$ | 54.72 | 3.45 | 7.98 | 54.72 | 3.53 | 8.04 |
| 46 | 200–205 | $C_{17}H_{15}Cl_2N_3O_2$ | 56.05 | 4.15 | 11.54 | 55.95 | 4.17 | 11.29 |
| 47 | 86–89 | $C_{19}H_{18}Cl_2N_2O_3$ | 58.02 | 4.61 | 7.12 | 58.16 | 4.76 | 7.32 |
| 48 | — | $C_{16}H_{12}Cl_2N_2O_3$ | 54.72 | 3.45 | 7.98 | 54.73 | 3.49 | 7.72 |
| 49 | 96–98 | $C_{17}H_{14}Cl_2N_2O_3$ | 55.90 | 3.86 | 7.67 | 57.13 | 4.30 | 9.28 |
| 50 | 182–183 | $C_{16}H_{12}Cl_2N_2O_3$ | 54.72 | 3.45 | 7.98 | 54.50 | 3.31 | 7.94 |
| 51 | oil | $C_{17}H_{14}Cl_2N_2O_3$ | 55.90 | 3.86 | 7.67 | 53.58 | 3.95 | 7.44 |
| 52 | 193–195 | $C_{16}H_{15}N_3OS$ | 64.62 | 5.08 | 14.13 | 64.37 | 5.28 | 14.07 |
| 53 | 238–240 | $C_{21}H_{17}N_3OS$ | 70.17 | 4.77 | 11.69 | 69.14 | 4.86 | 11.44 |
| 54 | 128.0–131.5 | $C_{16}H_{16}ClFN_2O_2$ | 56.73 | 4.76 | — | 56.85 | 4.98 | — |
| 55 | 149.5–151.0 | $C_{13}H_{14}FN_3O_2$ | 59.31 | 5.36 | — | 59.34 | 5.31 | — |
| 56 | 167.5–168.5 | $C_{13}H_{13}ClFN_3O_2$ | 52.45 | 4.40 | — | 51.90 | 4.37 | — |

The effectiveness of compounds representative of this invention as terrestrial herbicides were evaluated as preemergence herbicides and postemergence herbicides. The test plants were crabgrass, mustard, nightshade, teaweed, velvetleaf, foxtail, quackgrass and morningglory. For the preemergence test, seeds of the type of plants as shown in Table V were sown in fresh soil. In the preemergence test, the soil was sprayed with a solution of the test compound immediately after the seeds were planted. The solution was about a 1% by weight solution of the test compound in phytobland acetone or acetone/water mixtures. The compounds were applied at the rate of 8 lbs active ingredient/acre of soil surface.

Approximately three weeks after spray applications, the herbicidal activity of the compound was determined by visual observation of the treated areas in comparison with untreated controls. These observations are reported in Table V on a scale of 0 to 100% control of plant growth.

In the postemergence test, the soil and developing plants were sprayed about two weeks after the seeds were sown. The compounds were applied at the rate of 8 lbs active ingredient/acre from about a 1% by weight solution of the test compound in acetone. The postemergence herbicidal activity was measured in the same way as the preemergence activity at three weeks following treatment.

The results of both the preemergence and postemergence tests are set forth in Table V below:

TABLE V
BIOLOGICAL ACTIVITY OF HERBICIDAL CARBINOL CARBAMATES, UREAS, AND N-ALPHA SUBSTITUTED ACETYLCARBAMATES

| Ex. | Crab grass | Morningglory | Velvet leaf | Foxtail | Mustard | Night shade | Teaweed | Quack grass |
|---|---|---|---|---|---|---|---|---|
| | | | Pre-emergent Herbicidal Activity | | | | | |
| 1 | 100 | 100 | 100 | 100 | 100 | — | 100 | 100 |
| 2 | 100 | 100 | 100 | 100 | 100 | 100 | 100 | 100 |
| 3 | 93 | 100 | 100 | 92 | 100 | 100 | 100 | 100 |
| 4 | 0 | 0 | 0 | 0 | 0 | 0 | 0 | 0 |
| 5 | 0 | 0 | 99 | 12 | 100 | 100 | 100 | 100 |
| 6 | 0 | 0 | 12 | 0 | 0 | 0 | 0 | 0 |
| 7 | 46 | 52 | 100 | 86 | 100 | 72 | 100 | 30 |

TABLE V-continued
BIOLOGICAL ACTIVITY OF HERBICIDAL CARBINOL CARBAMATES, UREAS, AND N-ALPHA SUBSTITUTED ACETYLCARBAMATES

| Ex. | Crab grass | Morningglory | Velvet leaf | Foxtail | Mustard | Night shade | Teaweed | Quack grass |
|---|---|---|---|---|---|---|---|---|
| 8 | 0 | 100 | 42 | 72 | 100 | 0 | 65 | 55 |
| 9 | 0 | 0 | 98 | 0 | 0 | 0 | 74 | 0 |
| 10 | 91 | 98 | 100 | 99 | 100 | 100 | 100 | 26 |
| 11 | 0 | 12 | 78 | 6 | 100 | 0 | 54 | 20 |
| 12 | 100 | 100 | 100 | 97 | 100 | 100 | 100 | 100 |
| 13 | 6 | 32 | 100 | 12 | 100 | 100 | 46 | 35 |
| 14 | 65 | 100 | 100 | 71 | 100 | 72 | 100 | 30 |
| 15 | 0 | 12 | 6 | 0 | 0 | 0 | 12 | 0 |
| 16 | 42 | 54 | 100 | 65 | 100 | 100 | 100 | 10 |
| 17 | 42 | 100 | 100 | 62 | 100 | 100 | 100 | 20 |
| 18 | 30 | 100 | 100 | 82 | 100 | 46 | 0 | 10 |
| 19 | 12 | 0 | 100 | 30 | 71 | 0 | 6 | 100 |
| 20 | 100 | 0 | 100 | 100 | 100 | 100 | 26 | 72 |
| 21 | 0 | 0 | 0 | 0 | 0 | 0 | 0 | 0 |
| 22 | 84 | 100 | 100 | 54 | 100 | 100 | 100 | 75 |
| 23 | 6 | 30 | 100 | 12 | 100 | 12 | 12 | 100 |
| 24 | 62 | 100 | 100 | 88 | 100 | 100 | 100 | 100 |
| 25 | 100 | 100 | 100 | 100 | 100 | — | 100 | 100 |
| 26 | 100 | 65 | 100 | 100 | 100 | — | 100 | 100 |
| 27 | 100 | 62 | 86 | 35 | 100 | 0 | 0 | 100 |
| 28 | — | 0 | 100 | 65 | 100 | 56 | 0 | 100 |
| 29 | 100 | 100 | 100 | 100 | 100 | 98 | 100 | 30 |
| 30 | 0 | 0 | 0 | 0 | 0 | 0 | 6 | 0 |
| 31 | 0 | 0 | 6 | 0 | 12 | 0 | 6 | 0 |
| 32 | 6 | 0 | 12 | 6 | 88 | 0 | 0 | 0 |
| 33 | 0 | 0 | 0 | 0 | 12 | 0 | 0 | 0 |
| 34 | 6 | 0 | 6 | 0 | 100 | 6 | 12 | 0 |
| 35 | 12 | 0 | 98 | 12 | 56 | 0 | 56 | 10 |
| 36 | 0 | 0 | 65 | 0 | 100 | 0 | 100 | 0 |
| 37 | 0 | 0 | 0 | 0 | 70 | 0 | 0 | 0 |
| 38 | 0 | 0 | 35 | 0 | 65 | 12 | 0 | 0 |
| 39 | 12 | 6 | 100 | 42 | 86 | 12 | 30 | 0 |
| 40 | 0 | 90 | 56 | 0 | 100 | 0 | 0 | 100 |
| 41 | 96 | 100 | 100 | 100 | 100 | 100 | 100 | 40 |
| 42 | — | 0 | 0 | -0 | 0 | 0 | — | 0 |
| 43 | 42 | 0 | 0 | 0 | 56 | 0 | — | 0 |
| 44 | — | 0 | 26 | 0 | 12 | 0 | — | — |
| 45 | 0 | 0 | 0 | 0 | 0 | 0 | — | 0 |
| 46 | 0 | 0 | 0 | 0 | 0 | 0 | — | — |
| 47 | 0 | 0 | 0 | 0 | 0 | 0 | — | — |
| 48 | 72 | 0 | 0 | 0 | 54 | — | — | — |
| 49 | 6 | 0 | 0 | 0 | 0 | 0 | — | 0 |
| 50 | 20 | 0 | 100 | 0 | 0 | 0 | 94 | 0 |
| 51 | 74 | 20 | 0 | 12 | 100 | 6 | 0 | 0 |
| 52 | — | 0 | 0 | 0 | 30 | 0 | — | — |
| 53 | — | 0 | 0 | 65 | 0 | 0 | — | — |
| 54* | 20 | 45 | 86 | 20 | 100 | 30 | 72 | 60 |
| 55 | 0 | 0 | 30 | 0 | 6 | 0 | 33 | 0 |
| 56 | 0 | 0 | 75 | 0 | 100 | 54 | 55 | 0 |
| Post-emergent Herbicidal Activity | | | | | | | | |
| 1 | 6 | 20 | 65 | 0 | 22 | 100 | 20 | 0 |
| 2 | 0 | 0 | 26 | 0 | 0 | 32 | 22 | 0 |
| 3 | 0 | 0 | 32 | 0 | 0 | 6 | 0 | 0 |
| 4 | 0 | 0 | 0 | 0 | 0 | 10 | 10 | 0 |
| 5 | 0 | 10 | 78 | 0 | 0 | 100 | 59 | 0 |
| 6 | 0 | 0 | 0 | 0 | 72 | 0 | 6 | 0 |
| 7 | 0 | 0 | 0 | 0 | 2 | 2 | 0 | 0 |
| 8 | 0 | 0 | 10 | 0 | 0 | 32 | 38 | 0 |
| 9 | 0 | 6 | 59 | 0 | 0 | 26 | 20 | 0 |
| 10 | 0 | 22 | 58 | 0 | 33 | 88 | 38 | 10 |
| 11 | 0 | 10 | 0 | 0 | 10 | 54 | 10 | 0 |
| 12 | 0 | 35 | 100 | 0 | 32 | 78 | 10 | 0 |
| 13 | 0 | 10 | 40 | 0 | 45 | 45 | 20 | 0 |
| 14 | 0 | 35 | 38 | 0 | 54 | 80 | 50 | 0 |
| 15 | 0 | — | 35 | 0 | 32 | 30 | 53 | 0 |
| 16 | 0 | 0 | 54 | 0 | 26 | 54 | 72 | 0 |
| 17 | 0 | — | 50 | 0 | 44 | 80 | 78 | 0 |
| 18 | 0 | 42 | 30 | 0 | 40 | 100 | 45 | 20 |
| 19 | 0 | 0 | 0 | 0 | 74 | 12 | 0 | 0 |
| 20 | 32 | 0 | 73 | 0 | 100 | 100 | 20 | 20 |
| 21 | 0 | 0 | 12 | 0 | 20 | 12 | 20 | 0 |
| 22 | 0 | 0 | 38 | 35 | 45 | 100 | 44 | 10 |
| 23 | 12 | 0 | 38 | 0 | 40 | 100 | 55 | 0 |
| 24 | 6 | 19 | 100 | 6 | 100 | 100 | 97 | 10 |
| 25 | 76 | 26 | 88 | 22 | 100 | — | 94 | 10 |
| 26 | 80 | 6 | 88 | 87 | 88 | 100 | 87 | 40 |
| 27 | 0 | — | 20 | 0 | 20 | — | 26 | 0 |

TABLE V-continued
BIOLOGICAL ACTIVITY OF HERBICIDAL CARBINOL CARBAMATES, UREAS, AND N-ALPHA SUBSTITUTED ACETYLCARBAMATES

| Ex. | Crab grass | Morningglory | Velvet leaf | Foxtail | Mustard | Night shade | Teaweed | Quack grass |
|---|---|---|---|---|---|---|---|---|
| 28 | — | 26 | 100 | 94 | 100 | 100 | — | 20 |
| 29 | 0 | 33 | 93 | 6 | 50 | 100 | 46 | 0 |
| 30 | 0 | 0 | 0 | 0 | 0 | 0 | 0 | 0 |
| 31 | 0 | 0 | 6 | 0 | 0 | 0 | 12 | 0 |
| 32 | 0 | 0 | 12 | 0 | 100 | 0 | 50 | 0 |
| 33 | 0 | 0 | 20 | 0 | 0 | 0 | 10 | 0 |
| 34 | 0 | 0 | 0 | 0 | 0 | 0 | 0 | 0 |
| 35 | 0 | 0 | 14 | 0 | 12 | 40 | 6 | 0 |
| 36 | 0 | 6 | 12 | 0 | 32 | 26 | 26 | 0 |
| 37 | 0 | 0 | 0 | 0 | 32 | 10 | 0 | 0 |
| 38 | 0 | 0 | 26 | 0 | 45 | 72 | 30 | 0 |
| 39 | 0 | 0 | 45 | 0 | 14 | 32 | 33 | 0 |
| 40 | 0 | 0 | 54 | 0 | 95 | 56 | 100 | 0 |
| 41 | 100 | 100 | 95 | 100 | 100 | 100 | 100 | 0 |
| 42 | 0 | 72 | 0 | 0 | 56 | 20 | — | 0 |
| 43 | — | 0 | 0 | 0 | 0 | 0 | — | — |
| 44 | — | 0 | 10 | 0 | 0 | 0 | — | — |
| 45 | 0 | 0 | 10 | 0 | 12 | 0 | — | 0 |
| 46 | 0 | 30 | 0 | 0 | 12 | 0 | — | — |
| 47 | 0 | 0 | 0 | 0 | 12 | 0 | — | — |
| 48 | 0 | 0 | 6 | 0 | 72 | 0 | — | — |
| 49 | 0 | 0 | 20 | 0 | 6 | 6 | — | 0 |
| 50 | 0 | 6 | 20 | 0 | 30 | 56 | 42 | 0 |
| 51 | 0 | 12 | — | 74 | 74 | 90 | 74 | 0 |
| 52 | — | 0 | 0 | 0 | 0 | 0 | — | — |
| 53 | — | 0 | 0 | 0 | 0 | 0 | — | — |
| 54* | 6 | 12 | 55 | 0 | 12 | 40 | 59 | 30 |
| 55 | 0 | 0 | 0 | 0 | 0 | 0 | 0 | 0 |
| 56 | 0 | 0 | 0 | 11 | 0 | 0 | 0 | 0 |

*Tested at 4 lbs/acre

It will be understood that the plant species employed in the above tests are merely representative of a wide variety of plants that can be controlled by the use of the compounds of this invention. The compounds contemplated in this invention may be applied as postemergent and preemergent herbicides according to methods known to those skilled in the art. Compositions containing the compounds as the active ingredient will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, or nitrobenzene and dispersing the toxicants in water with the aid of suitable surface active emulsifying and dispersing agent.

The choice of dispersing and emulsifying agents and the amount employed is dictated by the nature of the composition and the ability of the agent to facilitate the dispersion of the compound. Generally, it is desirable to use as little of the agent as is possible, consistent with the desired dispersion of the compound in the spray so that rain does not re-emulsify the compound after it is applied to the plant and wash it off the plant. Nonionic, anionic, amphoteric or cationic dispersing and emulsifying agents may be employed; for example, the condensation products of alkylene oxides with phenol and organic acids, alkyl aryl sulfonates, complex ether alcohols, quaternary ammonium compounds, and the like.

Activity can often be enhanced by use of an emulsifiable crop oil such as Surfel, a trademark of the Union Carbide Corporation for a proprietary composition which comprises a phytobland mixture of surfactant and oil. The surfactant is a blend of polyoxyethylene ethers and the oil is a paraffinic petroleum distillate.

In preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the compound contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pounds of active ingredient per acre.

The herbicides contemplated herein have a high margin of safety in that when used in sufficient amount to control broadleaf weeds they do not burn or injure the crop and they resist weathering which includes wash-off caused by rain, decomposition by ultra-violet light, oxidation, or hydrolysis in the presence of moisture or, at least such decomposition, oxidation, and hydrolysis as would materially decrease the desired characteristic of the compound or impart undesirable characteristic for instance, phytotoxicity, to the compound. It will be appreciated that the compounds of this invention can also be used in combination with other biologically active compounds.

Although the invention has been illustrated by the foregoing examples, it is not to be construed as being limited to the materials employed therein; but rather, the invention encompasses the generic area as hereinafter disclosed. Various modifications and embodiments can be made without departing from the spirit and scope thereof.

What is claimed is:

1. A compound of the formula:

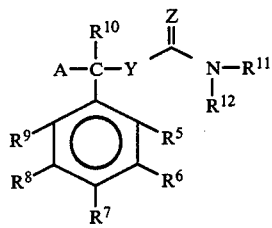

wherein:

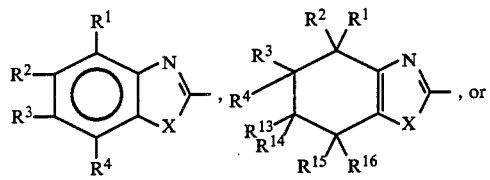

X is O, or NR;
Y is O, or S;
Z is O, or NR;
R is H or alkyl;
$R^1$ through $R^9$ inclusive and $R^{13}$ through $R^{16}$ inclusive are individually: hydrogen, halogen, alkyl, cycloalkyl, haloalkyl, halocycloalkyl, alkoxy, haloalkoxy, alkylthio, alkylamino, dialkylamino, nitro, cyano: or phenyl, phenoxy, or phenylthio unsubstituted or substituted with alkyl, alkoxy, alkylthio, halogen, nitro, cyano, amino, haloalkyl, alkylamino, dialkylamino, alkoxycarbonyl, alkylaminocarbonyl, dialkylaminocarbonyl, alkanoyl, aroyl, alkenyl, or alkynyl;
$R^{10}$ is hydrogen, alkyl, cycloalkyl, haloalkyl, halocycloalkyl, aryl, cyano, alkynyl; and
$R^{11}$ and $R^{12}$ are individually hydrogen, $C_1$-$C_3$ alkyl, $C_1$-$C_3$ haloalkyl, $C_1$-$C_3$ alkoxy, $C_1$-$C_3$ alkylthio: or phenoxy; unsubstituted or substituted with halo, alkyl, alkoxy, nitro, cyano, alkylthio, alkylamino; alpha-haloacetyl, acety, alpha-alkylthioacetyl, alpha-aminoacetyl, alpha-alkoxyacetyl, alpha-phosphonoacetyl, phosphinoacetyl, phosphinylacetyl, or propionyl.

2. A compound according to claim 1 wherein A is

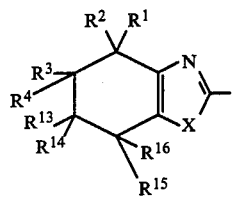

3. A compound according to claim 1 wherein A is

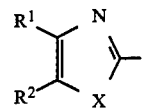

4. A compound of the formula:

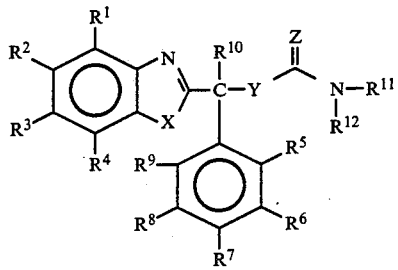

wherein:
X is O, or NR;
Y is O, or S;
Z is O, or NR;
R is H or alkyl;
$R^1$ through $R^9$ inclusive are individually: hydrogen, halogen, alkyl, cycloalkyl, haloalkyl, halocycloalkyl, alkoxy, haloalkoxy, alkylthio, alkylamino, dialkylamino, nitro, cyano: or phenyl, phenoxy, or phenylthio unsubstituted or substituted with alkyl, alkoxy, alkylthio, halogen, nitro, cyano, amino, haloalkyl, alkylamino, dialkylamino, alkoxycarbonyl, alkylaminocarbonyl, dialkylaminocarbonyl, alkanoyl, aroyl, alkenyl, or alkynyl;
$R^{10}$ is hydrogen, alkyl, cycloalkyl, haloalkyl, halocycloalkyl, aryl, cyano, alkynyl; and
$R^{11}$ and $R^{12}$ are individually hydrogen, $C_1$-$C_3$ alkyl, $C_1$-$C_3$ haloalkyl, $C_1$-$C_3$ alkoxy, $C_1$-$C_3$ alkylthio: or phenoxy; unsubstituted or substituted with halo, alkyl, alkoxy, nitro, cyano, alkylthio, alkylamino; alpha-haloacetyl, acetyl, alpha-alkylthioacetyl, alpha-aminoacetyl, alpha-alkoxyacetyl, alpha-phosphonoacetyl, phosphinoacetyl, phosphinylacetyl, or propionyl.

5. A compound according to claim 4 wherein:
$R^1$, $R^2$, $R^3$ and $R^4$ are hydrogen; and
X, Y and Z are O.

6. A compound according to claim 5 wherein $R^7$ and $R^{10}$ is hydrogen; and $R^5$, $R^6$, $R^8$, and $R^9$ are individually hydrogen, $C_1$-$C_3$ alkyl halogen or haloalkyl.

7. A compound according to claim 6 wherein:
$R^{11}$ and $R^{12}$ are individually hydrogen, $C_1$-$C_3$ alkyl, unsubstituted acetyl or halosubstituted acetyl.

8. A herbicidal composition comprising an acceptable carrier and a herbicidally effective amount of the compound of claim 1.

9. A herbicidal composition comprising an acceptable carrier and a herbicidally effective amount of the compound of claim 2.

10. A herbicidal composition comprising an acceptable carrier and a herbicidally effective amount of the compound of claim 3.

11. A herbicidal composition comprising an acceptable carrier and a herbicidally effective amount of the compound of claim 4.

12. A herbicidal composition comprising an acceptable carrier and a herbicidally effective amount of the compound of claim 5.

13. A herbicidal composition comprising an acceptable carrier and a herbicidally effective amount of the compound of claim 6.

14. A herbicidal composition comprising an acceptable carrier and a herbicidally effective amount of the compound of claim 7.

15. A method for the selective control of undesirable vegetation which comprises applying to the locus to be treated a herbicidally effective amount of the composition of claim 8.

16. A method for the selective control of undesirable vegetation which comprises applying to the locus to be treated a herbicidally effective amount of the composition of claim 9.

17. A method for the selective control of undesirable vegetation which comprises applying to the locus to be treated a herbicidaly effective amount of the composition of claim 10.

18. A method for the selective control of undesirable vegetation which comprises applying to the locus to be treated a herbicidally effective amount of the composition of claim 11.

19. A method for the selective control of undesirable vegetation which comprises applying to the locus to be treated a herbicidally effective amount of the composition of claim 12.

20. A method for the selective control of undesirable vegetation which comprises applying to the locus to be treated a herbicidally effective amount of the composition of claim 13.

21. A method for the selective control of undesirable vegetation which comprises applying to the locus to be treated a herbicidally effective amount of the composition of claim 14.

22. A compound according to claim 7, wherein: $R^{11}$ and $R^{12}$ are individually $C_1$–$C_3$ alkyl, with a maximum combined number of carbon atoms in $R^{11}$ plus $R^{12}$ of 3, unsubstituted acetyl or halo-substituted acetyl.

23. A compound according to claim 2, wherein $R^1 R^2$, $R^3$, $R^4$, $R^{13}$, $R^{14}$, $R^{15}$ $R^{16}$ are hydrogen.

* * * * *

UNITED STATES PATENT AND TRADEMARK OFFICE
CERTIFICATE OF CORRECTION

PATENT NO. : 4,592,774
DATED : June 3, 1986
INVENTOR(S) : Tai-Teh Wu; Jamin Huang; David T. Manning It is certified that error appears in the above-identified patent and that said Letters Patent is hereby corrected as shown below:

Col. 13, line 61 in the left hand margin "X' are" should be --X' is --.
Line 65 "Cl,-N" should be --Cl, or -N--.

Col. 16, line 24 "H." should be -- N. --.

Col. 18, line 8 "iminoeher" should be --iminoether--.

Col 19, line 7 in the second aromatic ring of the structural formula "$R_4$" should be -- $R_5$ --.

Col. 21, line 47 "filtrate" should be -- filtered --.

Col. 22, line 48 "$C_{1412}$" should be --$C_{14}H_{12}$--.
line 49 insert a semicolon after "5.18".

Signed and Sealed this

Tenth Day of March, 1987

*Attest:*

DONALD J. QUIGG

*Attesting Officer*   Commissioner of Patents and Trademarks